(12) United States Patent
Georgeson

(10) Patent No.: US 7,617,730 B2
(45) Date of Patent: Nov. 17, 2009

(54) ULTRASONIC INSPECTION AND REPAIR MODE SELECTION

(75) Inventor: Gary E. Georgeson, Federal Way, WA (US)

(73) Assignee: The Boeing Company, Chicago, IL (US)

( * ) Notice: Subject to any disclaimer, the term of this patent is extended or adjusted under 35 U.S.C. 154(b) by 500 days.

(21) Appl. No.: 11/427,108

(22) Filed: Jun. 28, 2006

(65) Prior Publication Data

US 2008/0000299 A1 Jan. 3, 2008

(51) Int. Cl.
G01N 29/06 (2006.01)
(52) U.S. Cl. ...................................................... 73/602
(58) Field of Classification Search ........................ None
See application file for complete search history.

(56) References Cited

U.S. PATENT DOCUMENTS

| | | | |
|---|---|---|---|
| 4,058,003 A | 11/1977 | Macovski | |
| 4,591,511 A * | 5/1986 | Peebles, Jr. | 427/142 |
| 4,596,145 A * | 6/1986 | Smith et al. | 73/626 |
| 4,869,109 A * | 9/1989 | Miglianico et al. | 73/602 |
| 4,881,177 A * | 11/1989 | McClean et al. | 700/258 |
| 5,073,814 A | 12/1991 | Cole, Jr. et al. | |
| 5,091,893 A | 2/1992 | Smith et al. | |
| 5,165,270 A | 11/1992 | Sansalone et al. | |
| 5,614,670 A | 3/1997 | Nazarian et al. | |
| 5,680,863 A | 10/1997 | Hossack et al. | |
| 5,735,282 A | 4/1998 | Hossack | |
| 5,814,731 A | 9/1998 | Alexander et al. | |
| 5,983,701 A | 11/1999 | Hassani et al. | |
| 6,234,025 B1 * | 5/2001 | Gieske et al. | 73/642 |
| 6,424,597 B1 | 7/2002 | Bolomey et al. | |
| 6,476,541 B1 | 11/2002 | Smith et al. | |
| 6,586,702 B2 | 7/2003 | Wiener-Avnear et al. | |
| 6,591,679 B2 * | 7/2003 | Kenefick et al. | 73/597 |
| 6,598,485 B1 | 7/2003 | Lin et al. | |
| 6,656,124 B2 | 12/2003 | Flesch et al. | |
| 6,681,466 B2 * | 1/2004 | David et al. | 29/402.01 |
| 6,691,576 B1 * | 2/2004 | Sato et al. | 73/601 |
| 6,777,931 B1 * | 8/2004 | Takada et al. | 324/240 |
| 6,798,717 B2 | 9/2004 | Wiener-Avnear et al. | |
| 6,822,374 B1 | 11/2004 | Smith et al. | |
| 2002/0128790 A1 * | 9/2002 | Woodmansee | 702/81 |
| 2004/0123665 A1 | 7/2004 | Blodgett et al. | |
| 2005/0132809 A1 * | 6/2005 | Fleming et al. | 73/597 |
| 2006/0004499 A1 * | 1/2006 | Trego et al. | 701/29 |

(Continued)

OTHER PUBLICATIONS

*Flexible Ultrasonic Arrays*, HD Laboratories, Inc., NDT and Electronic Engineers;2 pages, available at http://www.hdlabs.com/NDT/FlexibleArrays/flexiblearrays.htm; Apr. 28, 2006; publicly available on or before Sep. 1, 2005; 2 pages.

(Continued)

*Primary Examiner*—Hezron Williams
*Assistant Examiner*—Rose M Miller
(74) *Attorney, Agent, or Firm*—Alston & Bird LLP

(57) ABSTRACT

In a method of inspecting a structure, a two-dimensional array of sensors is disposed onto a surface, ultrasonic pulses are sent into the surface, and echo signals are received. An image of damage within the structure is graphically displayed, a determination of whether the damage satisfies a predetermined criterion is made, and a mode of returning the structure to usage or service is selected. The predetermined criterion may define a length, a depth, and an area. A-scan, B-scan, and C-scan images of the damage may be displayed. Threshold images may be displayed wherein each pixel of a matrix of pixels is colored one of only two colors.

32 Claims, 10 Drawing Sheets

U.S. PATENT DOCUMENTS

2006/0186260 A1* 8/2006 Magnuson et al. .......... 244/1 R

OTHER PUBLICATIONS

*General Provisions For Boeing (Buyer) Purchase Contract to Seller (Seller) for Flexible Ultrasonic Array Demonstration Unit*, privately exchanged between Buyer and Seller on approximately Mar. 24, 2004, never published, redacted copy 6 pages.

*SonoFlex™ Flexible Ultrasonic Array Systems*, The Boeing Company, Seattle, WA, publicly available at the Aging Aircraft Conference in Atlanta, Mar. 7-9, 2006, 1 page.

Jocelyn Langlois and R.S. Frankle, *Use of Flexible Ultrasonic Arrays in Inspection*, NDT.NET—Mar. 1999, vol. 4, No. 3, 5 pages.

* cited by examiner

ULTRASONIC INSPECTION AND REPAIR MODE SELECTION

FIELD OF THE INVENTION

Embodiments of the present invention relate generally to methods for inspecting structures. More particularly, embodiments of the invention relate to methods for determining whether damage satisfies criteria for different levels of repair, and selecting modes of returning a structure to usage.

BACKGROUND OF THE INVENTION

Non-destructive inspection (NDI) of structures involves examining a structure without harming the structure or requiring significant disassembly. Non-destructive inspection is typically preferred to avoid the time and costs associated with the removal of a part for inspection and to avoid the potential for causing damages when inspection is needed. Non-destructive inspection is used in the aircraft industry to inspect aircraft structures such as composite structures and bonded panels. Inspections may identify defects such as cracks, discontinuities, disbonds between layers, voids, and areas having undesirable porosity. Preventive inspections may be performed during manufacturing and at any time during the service life of an aircraft structure to validate the integrity and fitness of the structure. Inspections may also be prompted by incidents such as collisions and ballistic impacts that are suspected or known to cause damages.

Various types of ultrasonic methods are used to perform non-destructive inspections. For example, a structure may be inspected by a pulse-echo (PE) method wherein a sensor device sends ultrasonic pulses into a structure and receives echo pulses that reveal the condition of the structure. Data acquired by such a sensor device can be processed and presented to an operator. B-scan images can be produced that reveal depth characteristics of an inspected structure. C-scan images can be produced to reveal a mapping of the inspected structure. These images can reveal features that are not easily perceived or characterized by simple visual inspection of the exterior of a structure. Collecting data for B-scan and C-scan images typically entails physically moving a sensor along a portion of a structure in order to collect data across an area of the inspected structure. Thus, collecting data for such images can be time-consuming and physically challenging activities.

An ultrasonic sensor can be moved over a structure manually by a trained technician. For example, the technician may move a sensor side-to-side along one axis in order to collect data for a B-scan image. The technician may move a sensor along two axes in order to collect data for a two-dimensional mapping such as a C-scan image. The quality of the inspection depends significantly upon the performance of the technician. Thus, manual scanning of structures is time-consuming, labor-intensive, and prone to human error.

Automated inspection systems have been developed at least in part to relieve technicians of the challenges of manually moving inspection sensors across a structure. For example, the Automated Ultrasonic Scanning System (AUSS®) system includes a complex mechanical scanning system that can perform through-transmission ultrasonic (TTU) inspections. The AUSS system has robotically controlled probe arms that can be moved along opposing surfaces of a structure. Typically, one probe arm moves an ultrasonic transmitter along one surface of a structure, and another probe arm moves an ultrasonic receiver along the opposite surface in concert such that the transmitter and receiver are kept in alignment. To maintain the alignment, a complex positioning system provides motion control in numerous axes. Thus, typical AUSS systems include robotic components and control systems that can be expensive to obtain and challenging to set up and use for any given inspection. Furthermore, access to both sides of a structure must be available if the structure is to be inspected by TTU methods.

Two-dimensional arrays of ultrasonic pulse-echo sensors have been developed and employed in medical imaging procedures. Such arrays provide numerous sensors regularly distributed across an area and each sensor can collect location-specific data. Thus, a mapping of a portion of the interior anatomy of a medical patient can be obtained without movement of the sensors.

It would be advantageous to provide non-destructive inspection methods for inspecting a structure by disposition of a sensor array across an area of the structure without further movement of the array. It would be advantageous to provide one-sided inspection methods for detecting and characterizing damage beneath exterior surfaces of contoured structures such as aircraft wings and fuselages, bridge columns, and boat hulls. Furthermore, it would be advantageous to provide methods of applying pre-determined criteria in selecting a mode of returning a structure to usage, for example returning an aircraft structure to flying service.

BRIEF SUMMARY OF THE INVENTION

Embodiments of the invention may address at least some of the above needs and achieve other advantages. For example, an aspect of the invention relates to a method of inspecting an aircraft structure. The inventive method includes the steps of disposing a two-dimensional array of sensors onto a surface of an aircraft structure, sending ultrasonic pulses into the surface, receiving echo signals, graphically displaying an image of damage within the structure, determining whether the damage satisfies a predetermined criterion, and selecting a mode of returning the aircraft structure to flying service based on the determination of whether the damage satisfies a predetermined criterion.

The predetermined criterion may define a linear dimension such as a predetermined length, and determining whether the damage satisfies the criterion may entail determining whether a longest chord measurement of the damage exceeds the predetermined length. The predetermined criterion may also define a predetermined depth or area, and determining whether the damage satisfies the criterion may entail determining whether a measured depth or area of the damage exceeds the criterion.

Displaying an image of the damage may include displaying an echo amplitude C-scan image wherein each pixel of a matrix is colored to represent an amplitude of an echo signal received by a sensor to which the pixel uniquely corresponds. Displaying an image of the damage may also include displaying a depth C-scan image wherein each pixel of a matrix is colored to represent the time of flight of an echo pulse. Furthermore, displaying an image of the damage can also include displaying B-scan images. Threshold images may be displayed wherein each pixel of a matrix of pixels is colored one of only two colors.

At least one inventive method further includes making a repair to the damage according to the selected mode, disposing an ultrasonic sensor onto the surface of the aircraft structure at the location of the repair, graphically displaying an image of the repair, and determining the quality of the repair based on the displayed image. Determining the quality of the repair may entail determining whether an additional repair is needed, and the method may further include making an additional repair. Subsequently, an inspection sensor may be disposed at the location of the additional repair.

Another aspect of the invention relates to a method of inspecting a structure. The inventive method includes the steps of disposing a two-dimensional array of sensors onto a surface of a structure, sending ultrasonic pulses into the surface, receiving echo signals, graphically displaying an image of damage within the structure, determining whether the damage satisfies a predetermined criterion, and selecting a mode of returning the structure to usage based on the determination of whether the damage satisfies a predetermined criterion.

The structure may be a composite structure such as a bridge. Selecting a mode of returning the structure to usage may include selecting a mode of repairing the damage. At least one inventive method includes making a repair according to the selected mode of repairing, and permitting vehicle traffic to pass over or under the bridge. An additional repair may be made at a time when vehicle traffic is low.

The structure may be a composite structure such as a boat. Disposing the array onto a surface of the structure may include disposing the array onto the leading edge of a hull of a boat. The array can be disposed onto a surface of the boat while the boat floats in water.

BRIEF DESCRIPTION OF THE SEVERAL VIEWS OF THE DRAWINGS

Figure 1:
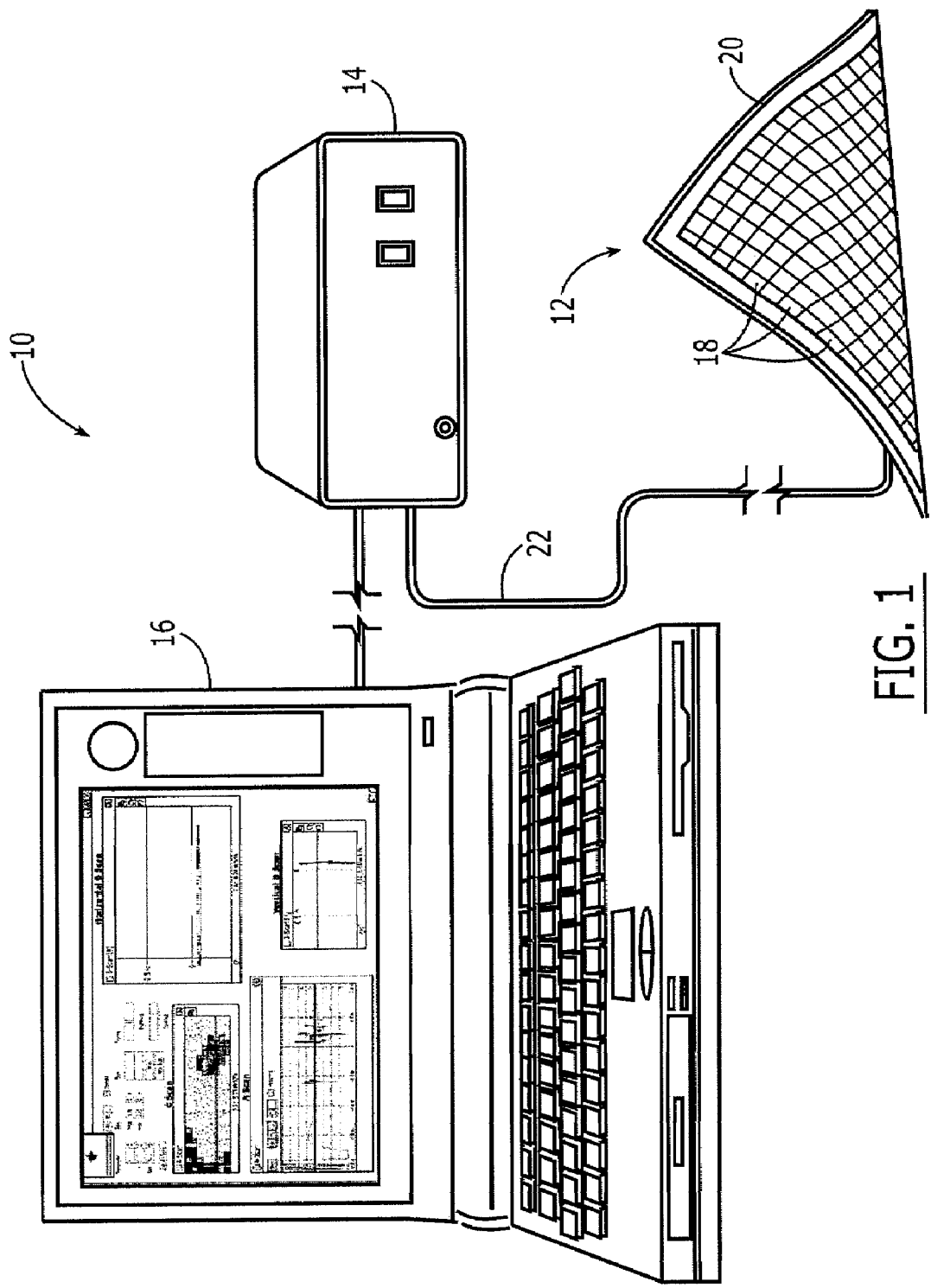
Figure 2:
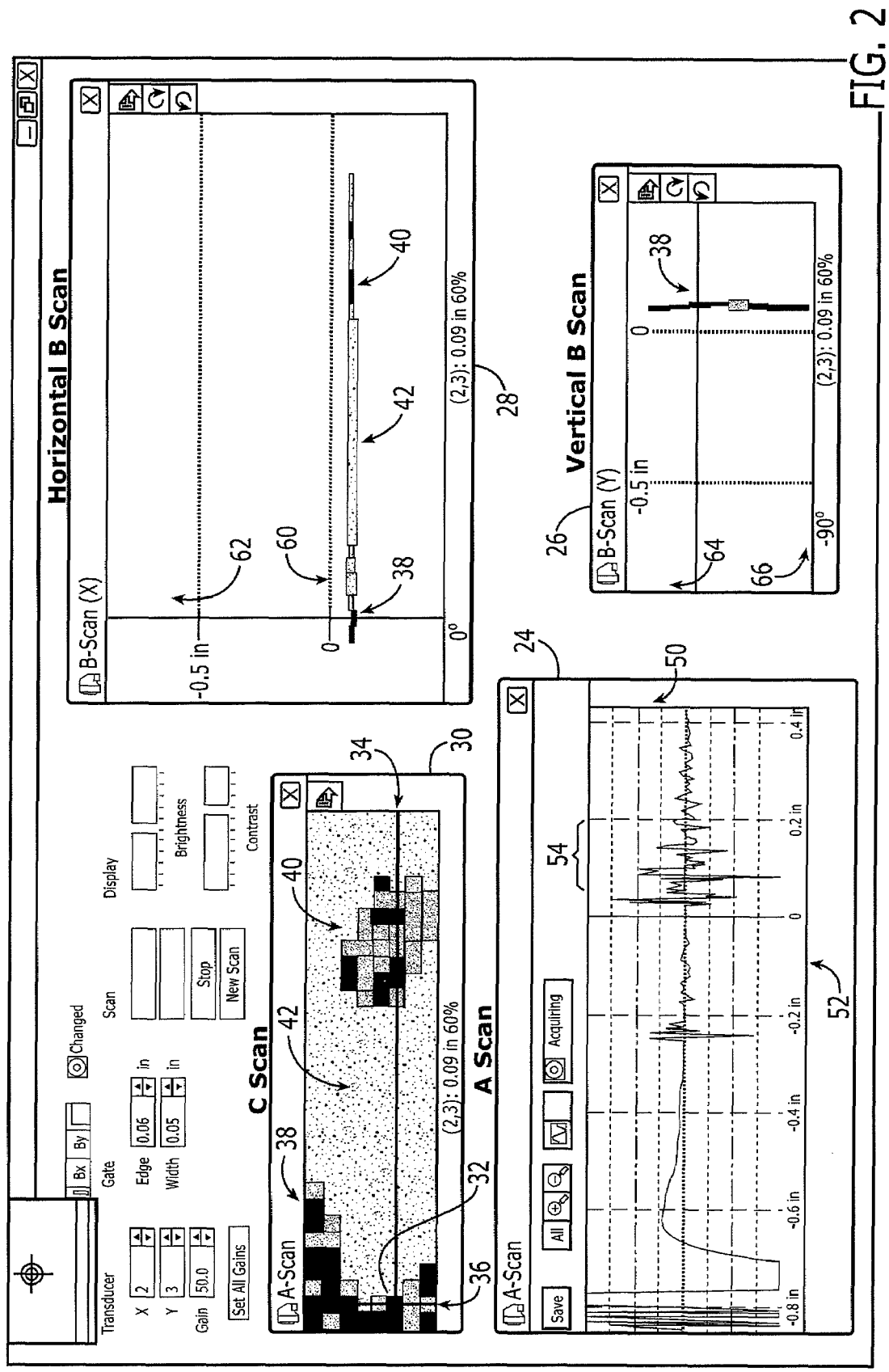
Figure 3:
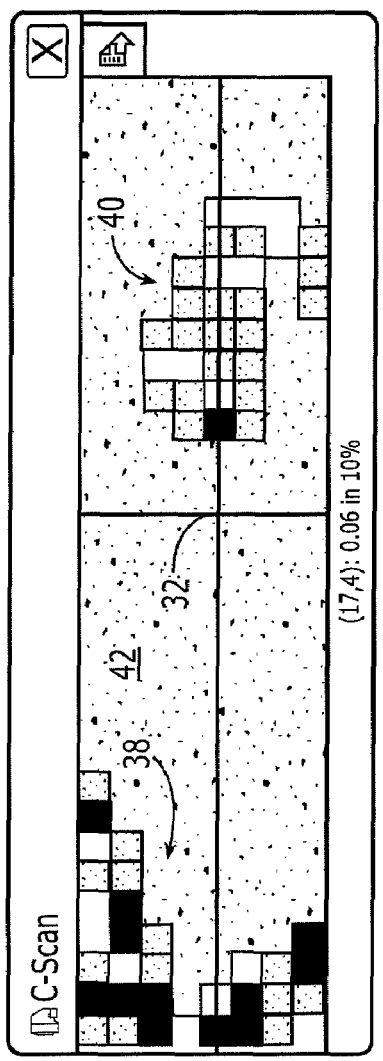
Figure 4:
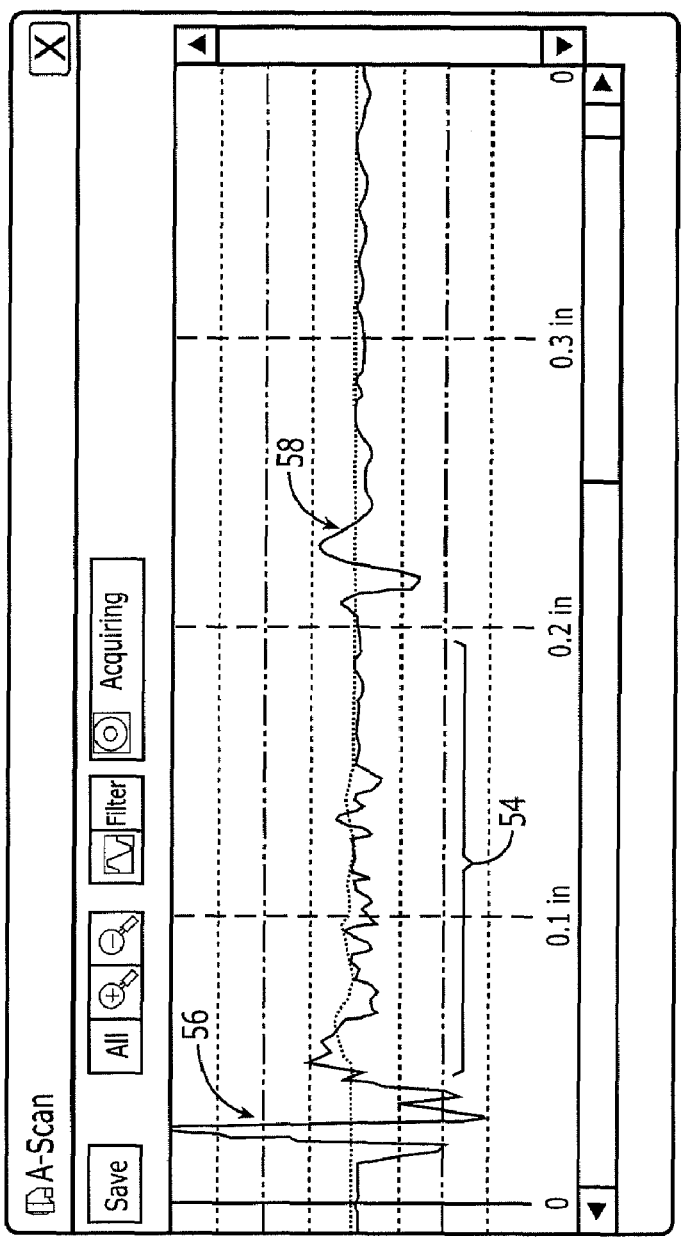
Figure 5:
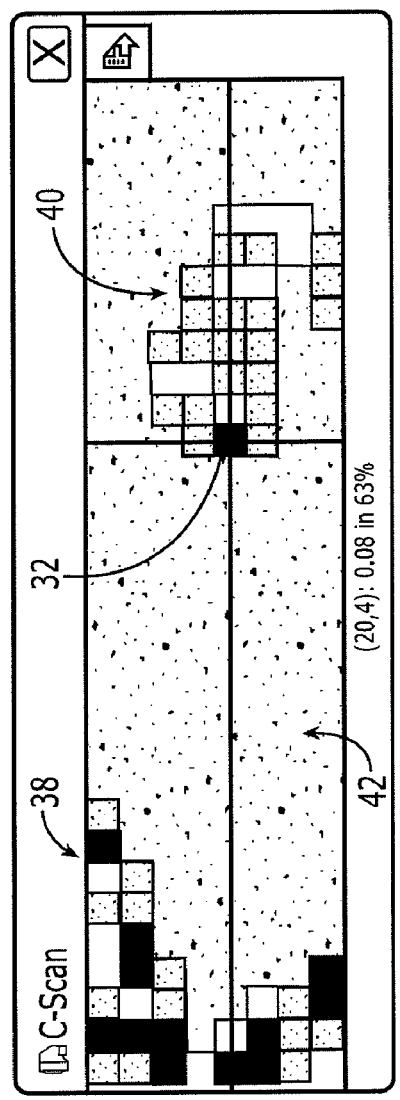
Figure 6:
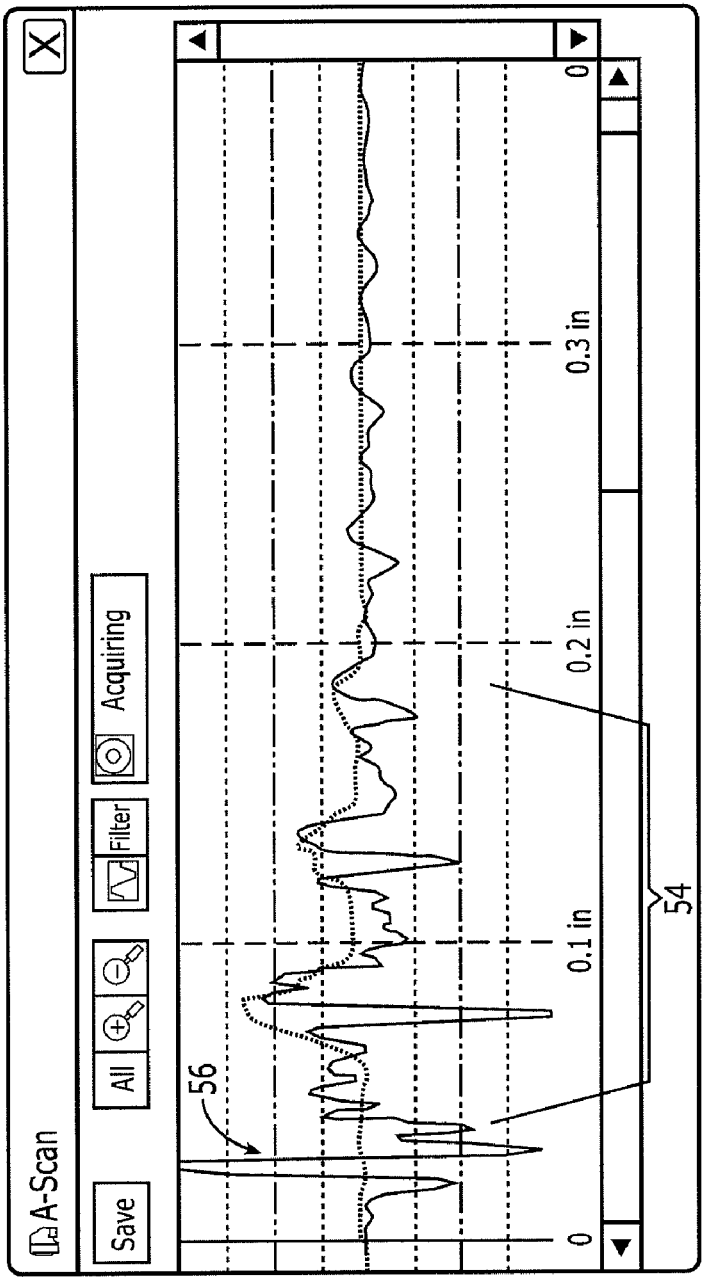
Figure 8:
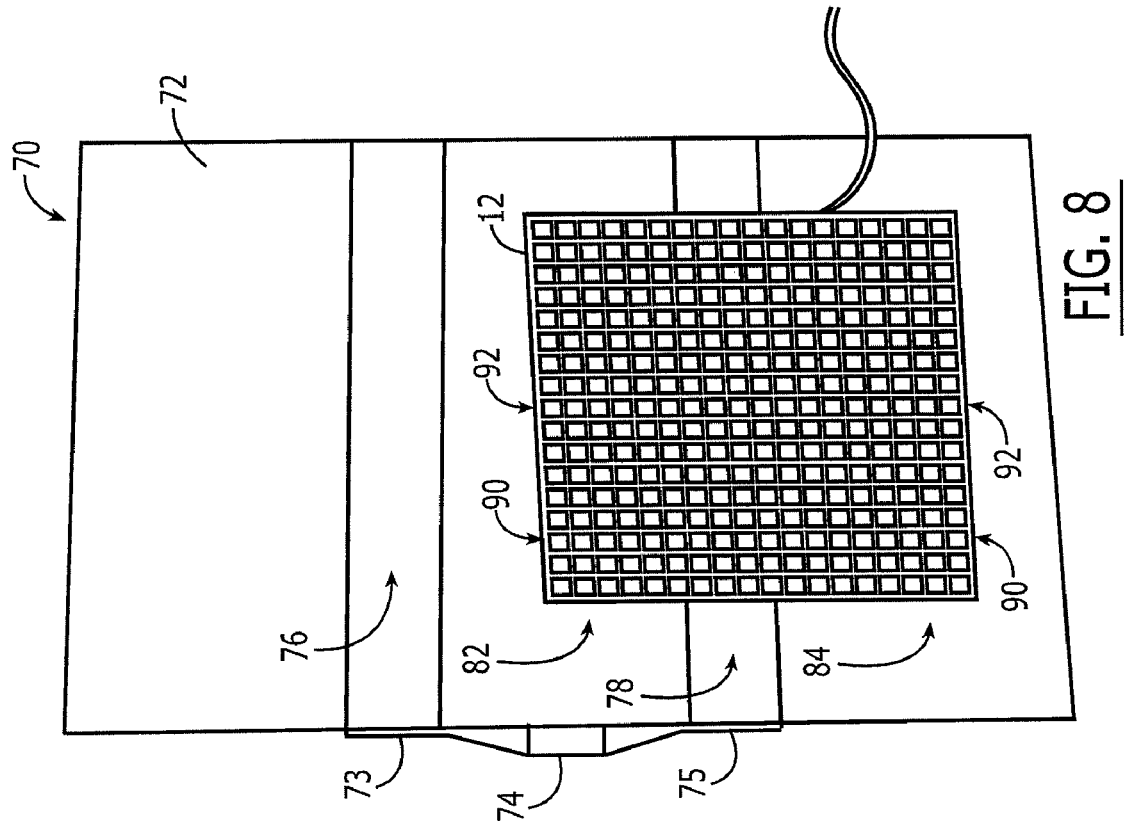
Figure 7:
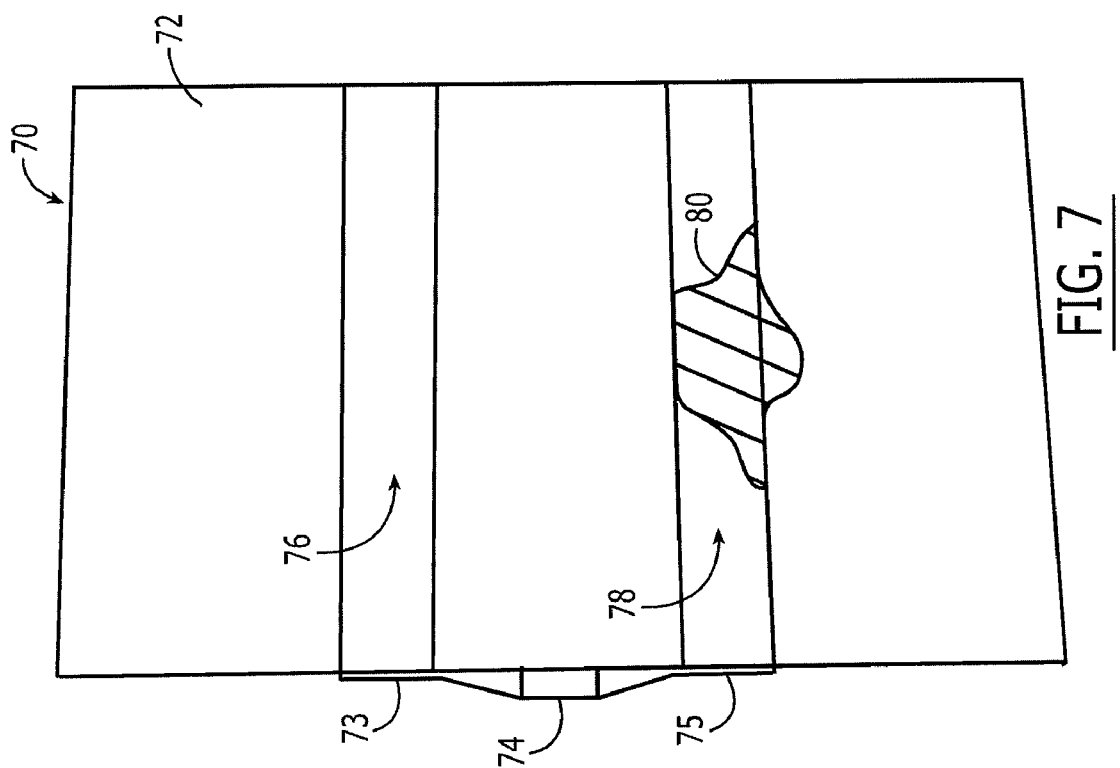
Figure 9:
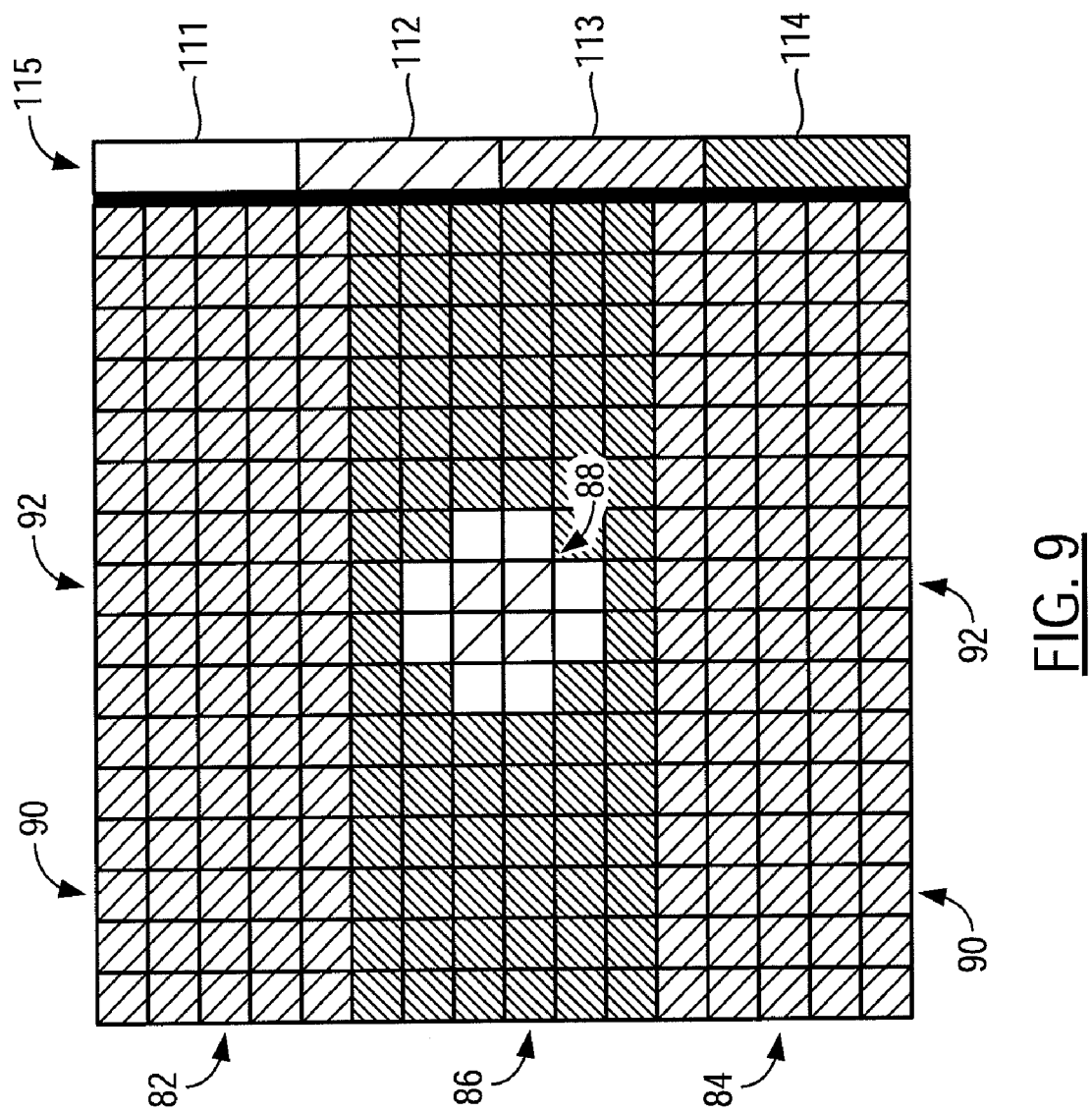
Figure 11:
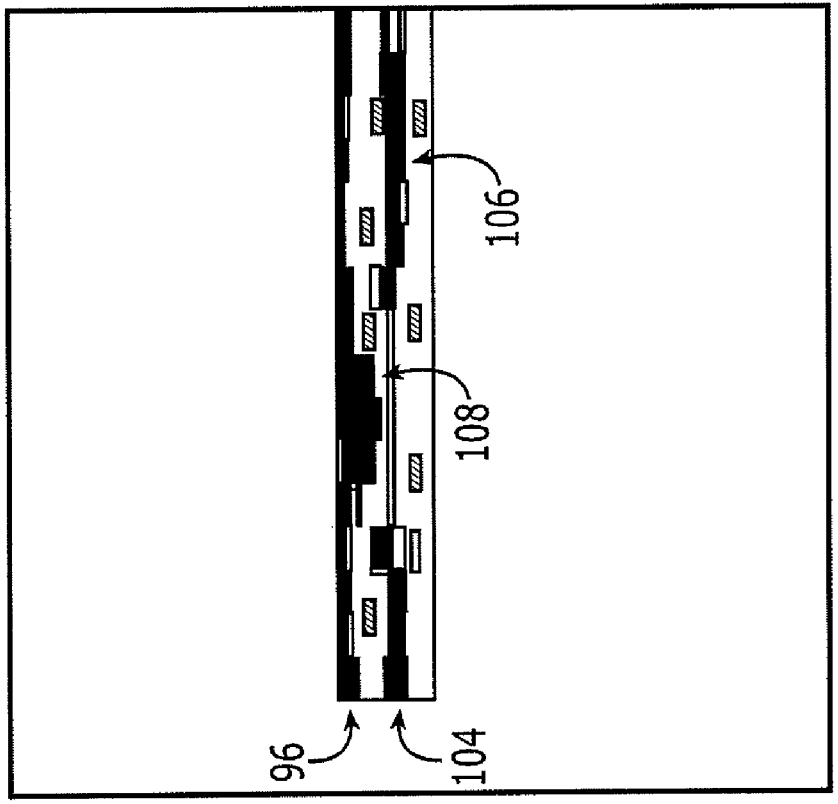
Figure 10:
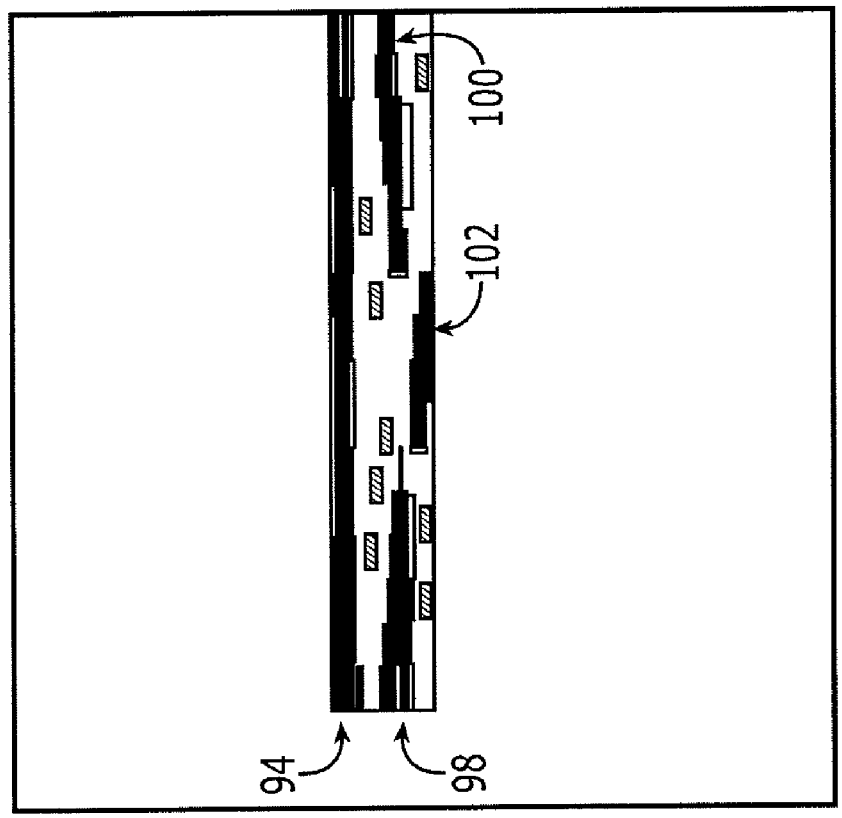
Figure 13:
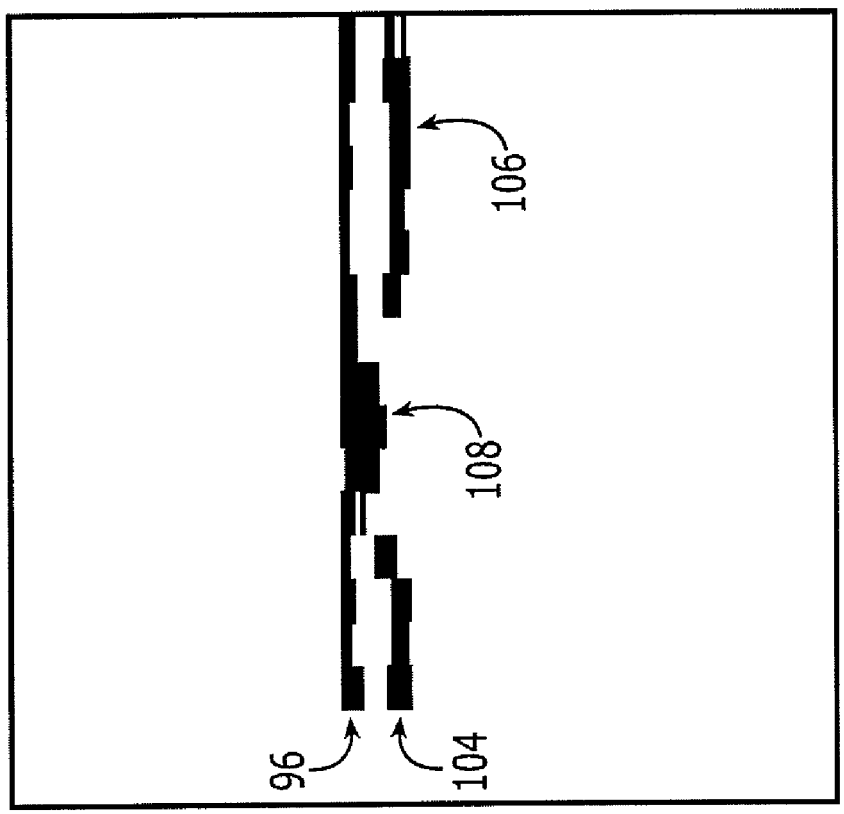
Figure 12:
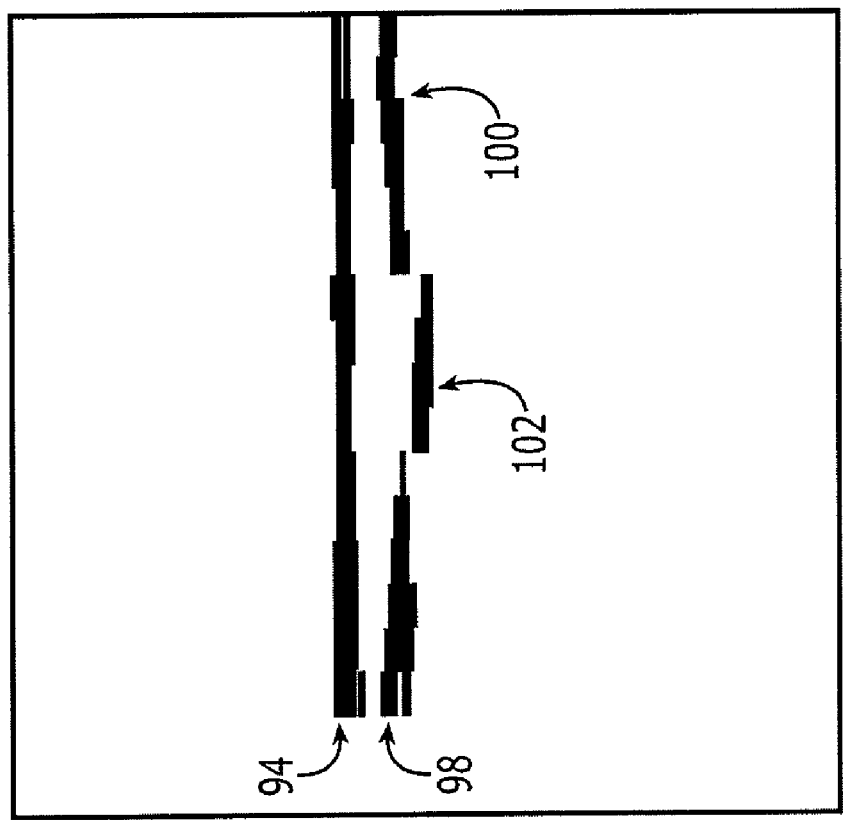
Figure 14:
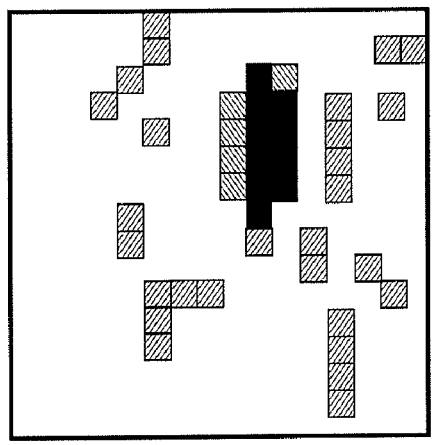
Figure 15:
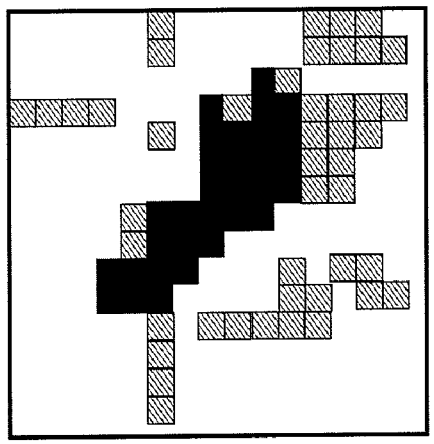
Figure 16:
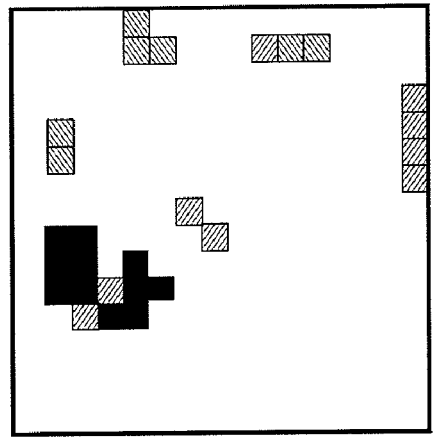
Figure 17:
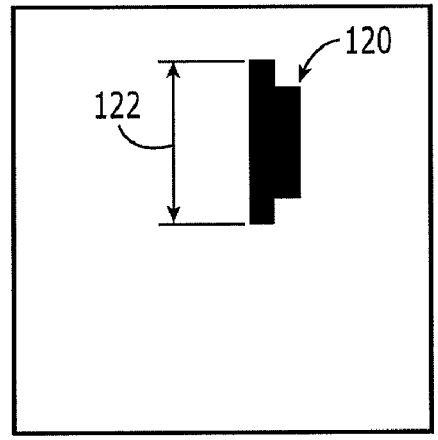
Figure 18:
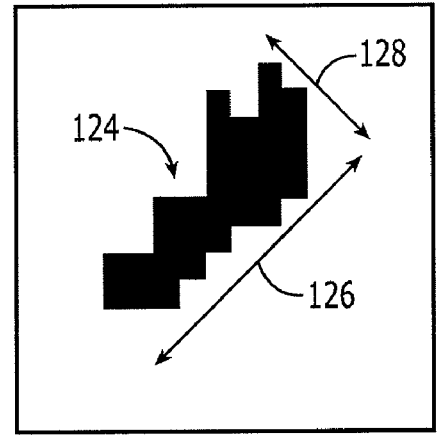
Figure 19:
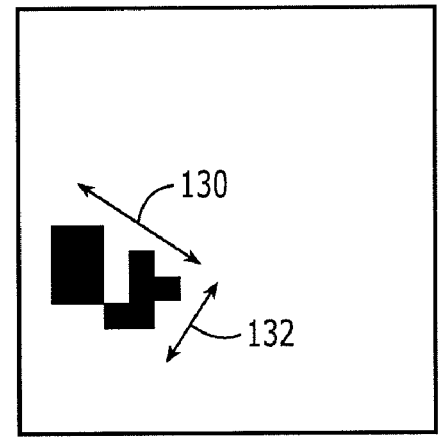
Figure 20:
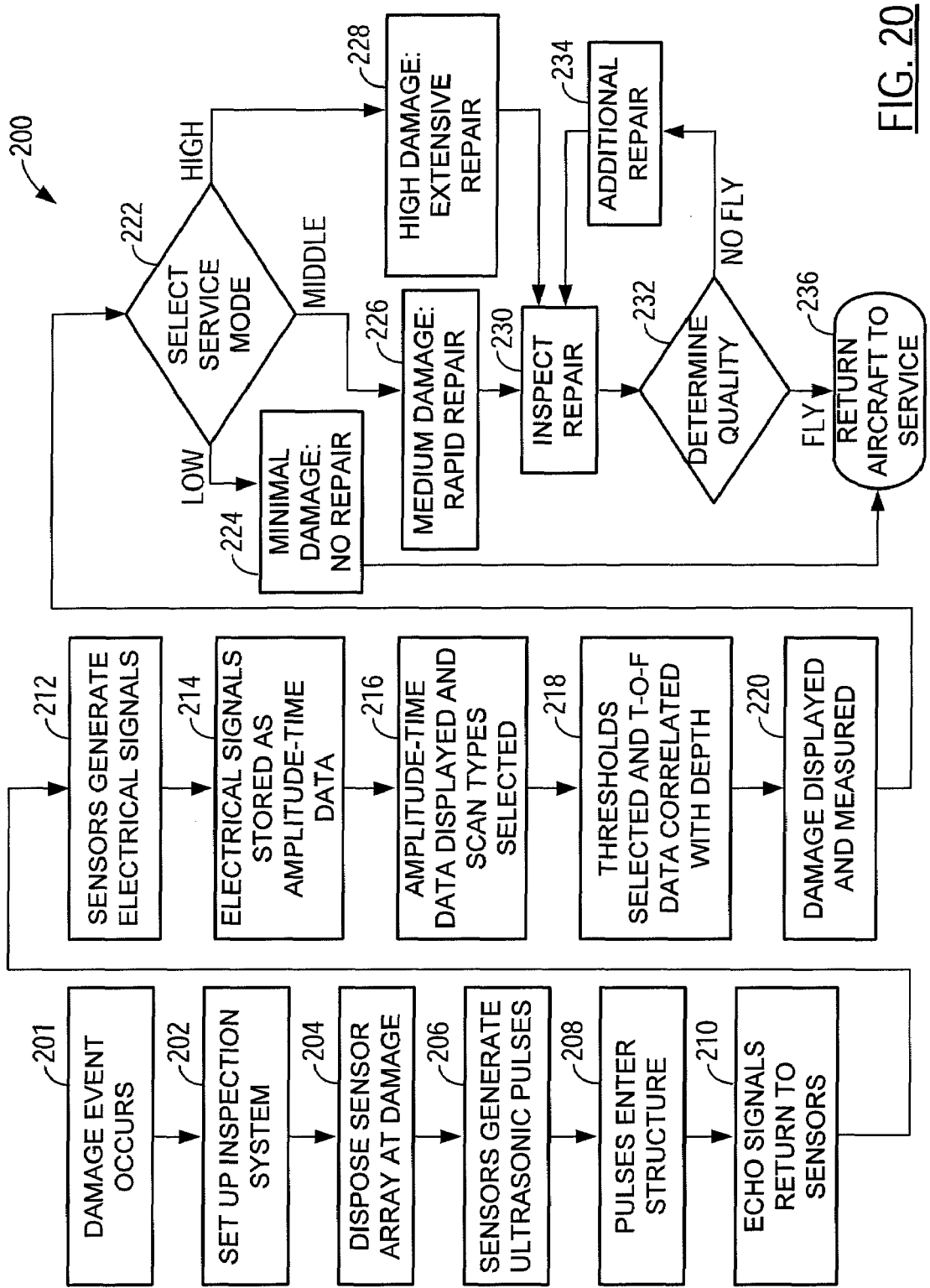

Having thus described the invention in general terms, reference will now be made to the accompanying drawings, which are not necessarily drawn to scale, and wherein:

FIG. 1 is a front view of an ultrasonic inspection system, which includes a flexible sensor array, by which an aircraft structure may be inspected by a method in accordance with one or more embodiment of the present invention;

FIG. 2 shows simulated A-scan, B-scan, and C-scan windows displaying simulated time and amplitude data related to inspecting a structure in accordance with one or more embodiment of the present invention;

FIG. 3 shows the simulated C-scan image of FIG. 2 with the cross-hair cursor therein disposed at a pixel corresponding to a sensor disposed at an undamaged structure location;

FIG. 4 shows a simulated A-scan waveform plot representing data collected by the sensor at the undamaged sensor location corresponding to the cursor position in FIG. 3;

FIG. 5 shows the simulated C-scan image of FIG. 2 with the cross-hair cursor therein disposed at a pixel corresponding to a sensor disposed at a damaged structure location;

FIG. 6 shows a simulated A-scan waveform plot representing data collected by the sensor at the undamaged sensor location corresponding to the cursor position in FIG. 5;

FIG. 7 is a perspective view of a damaged composite panel portion of an aircraft structure;

FIG. 8 is a perspective view of the composite panel of FIG. 7 with the flexible sensor array of FIG. 1 disposed across a damaged portion of the panel;

FIG. 9 is a simulated C-scan image representing data generated by disposition of the sensor array across the panel as shown in FIG. 8;

FIG. 10 is a simulated B-scan image, representing data generated by disposition of the sensor array across the panel as shown in FIG. 8, showing an undamaged columnar portion of the panel;

FIG. 11 is a simulated B-scan image, representing data generated by disposition of the sensor array across the panel as shown in FIG. 8, showing a damaged columnar portion of the panel;

FIG. 12 is a simulated B-scan threshold image corresponding to FIG. 10;

FIG. 13 is a simulated B-scan threshold image corresponding to FIG. 11;

FIG. 14 is a simulated C-scan image of a portion of an inspected aircraft structure, the image showing simulated features including an elongate damage;

FIG. 15 is another simulated C-scan image of another portion of an inspected aircraft structure, the image showing simulated features including damage distributed across an area;

FIG. 16 is a simulated C-scan image of yet another portion of an inspected aircraft structure, the image showing simulated features including a damage cluster;

FIG. 17 is a simulated C-scan threshold image corresponding to FIG. 14, wherein a longest chord of the simulated damage is measured;

FIG. 18 is a simulated C-scan threshold image corresponding to FIG. 15, wherein perpendicular chords are measured to determine an area encompassing the simulated damage;

FIG. 19 is a simulated C-scan threshold image corresponding to FIG. 16, wherein chords are measured to determine an area encompassing the simulated damage cluster; and FIG. 20 is a flowchart representation of a method of inspecting an aircraft structure according to an embodiment of the present invention.

DETAILED DESCRIPTION OF THE INVENTION

The present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

An ultrasonic inspection system 10 by which a structure, such as an aircraft structure or component, may be inspected according to at least one embodiment of the present invention is shown in FIG. 1. The ultrasonic inspection system 10 includes a flexible sensor array 12, an array controller 14, and a computing and display device 16. The flexible sensor array 12 comprises ultrasonic sensors 18 bonded to a flexible mat 20 in a regularly spaced pattern. Each ultrasonic sensor comprises a transducer element that is operable as a pulse-echo inspection sensor that both sends and receives ultrasonic waves. Such sensors are commercially available. The transducer elements can be fabricated, for example and as known, from a polymer-based piezo-electric material called polyvinylidene fluoride (PVDF).

The periphery of the flexible mat 20 may define a gasket for contacting an inspected structure and tentatively adhering the flexible sensor array to the structure when intervening air is removed by an optional vacuum system accessory of the ultrasonic inspection system 10. Alternatively, the flexible mat can be taped or otherwise tentatively adhered to an inspected structure by an adhesive material. Additionally, the flexible mat can be held in place by hand or by a clamp or bracket.

The sensor array 12 is illustrated in FIG. 1 to include two hundred and fifty six sensors disposed in rows and columns regularly spaced by one quarter of one inch to define a square grid pattern that is four inches wide on each side thereof. It should be understood that these descriptions relate nonetheless to sensor arrays having other numbers of sensors, other disposition patterns, and other pattern spacings. For example, these descriptions relate as well to a sensor array having one thousand and twenty fours sensors arranged in rows and columns regularly spaced by one quarter of one inch to define a square grid pattern that is eight inches wide on each side thereof. For further example these descriptions relate to sensor arrays defining hexagonal patterns and other patterns. Thus, these descriptions relate to a sensor array having any number of sensors arranged in any two-dimensional pattern.

The sensor array 12 is disposed in electronic communication with the array controller 14, for example by way of a cable 22 that can include any number of electrically conductive wires or by way of wireless communications. The array controller generally energizes each ultrasonic sensor 18 to send an ultrasonic pulse into an inspected structure and then receives an electrical signal generated by the sensor when an ultrasonic echo signal returns from the structure. Ultrasonic pulses traveling through a structure tend to reflect from surfaces, edges, and other discontinuities such as damages in the structure. A returning ultrasonic echo signal can include multiple time-distributed echo pulses reflected from surfaces and edges that are expected and from damage that deserves investigation and repair. The electrical signal generated by the sensor conveys amplitude and time data corresponding to the amplitudes and arrival times of echo pulses within the ultrasonic echo signal. The amplitude and time data can be used to discern damage related echo pulses from echo pulses reflected from undamaged features of a structure. After the controller energizes a sensor and collects amplitude and time data therefrom, a brief period of quiescence then passes before the controller energizes another sensor. By maintaining pulse-echo operations of each sensor separate in time from operations of each other sensor, cross-talk among the sensors is avoided and the data collected from each sensor can be associated with each sensor location. Thus, when the sensor array 12 is disposed against a structure, the data collected from the sensors can be associated with localized properties of the structure at the respective sensor locations.

The computing and display device 16 receives the collected amplitude and time data from the array controller 14 and graphically displays the data for interpretation by a user toward identifying damages in an inspected structure. For example, in FIG. 2 the computing and display device displays simulated data from a sensor array having rows and columns of sensors. In particular, FIG. 2 displays a simulated waveform plot from a particular sensor in an A-scan window 24, a simulated cross-section depth image from a column of sensors in a vertical B-scan window 26, a simulated cross-section depth image from a row of sensors in a horizontal B-scan window 28, and a simulated echo-amplitude image taken across a portion of the sensor array in a C-scan window 30.

The A-scan, B-scan, and C-scan images in FIGS. 1-6 and 9-19 are simulated images in that simulated data is graphically displayed in order to represent real data collected by a real sensor array. While some of these images are based at least in part on real data, they should be viewed as illustrations fabricated and provided to support understandings of embodiments of the invention. Further statements toward the simulated nature of these images are not present in the following descriptions for the sake of brevity. Nonetheless, all A-scan, B-scan, and C-scan images described herein should be understood as simulated images.

The simulated data shown in the displays of FIG. 2 represent real data generated by use of a flexible sensor array having at least two hundred and fifty six sensors disposed along at least eight rows and at least thirty two columns as evident in the regularly spaced two-dimensional rectangular matrix of pixels in the C-scan window 30. Each particular pixel of the C-scan window corresponds to a particular sensor, in a one-to-one correspondence. A cross-hair cursor 32 is disposed at a particular pixel arranged along a row 34 that corresponds to a row of sensors, and along a column 36 that corresponds to a column of sensors. Thus, the pixel under the cross-hair cursor corresponds to a particular location of an inspected structure, and the C-scan window 30 displays an image of an area of a structure inspected by disposition of a flexible sensor array across the area. The C-scan image includes images of damaged portions 38 and 40 of the inspected structure as distinguished by pixel colorations from an undamaged background area 42 corresponding to an undamaged area of the structure. The B-scan window 28 displays a B-scan cross-section depth image of the damaged portions 38 and 40 as derived from data collected by the row of sensors corresponding to the pixel row 34 in the C-scan image. Similarly, the B-scan window 26 displays a B-scan cross-section depth image of the damaged portion 38 as derived from data collected by the column of sensors corresponding to the pixel column 36.

An understanding of the C-scan image FIG. 2 may be gained by considering the A-scan window 24. A particular sensor, which corresponds to the pixel under the cross-hair cursor 32 in C-scan window 30, sent an ultrasonic pulse into a structure and an ultrasonic echo signal returned to the sensor. The sensor received the echo signal and generated an electrical signal as represented by the waveform plot that represents signal amplitude on a vertical axis 50 and time on a horizontal axis 52 in the A-scan window 24. The C-scan window 28 displays an echo amplitude C-scan image in that the coloration of each pixel therein corresponds to an amplitude of a portion of an echo signal. In particular, the coloration of the pixel under the cross-hair cursor 32 in the C-scan window relates to the amplitudes of echo pulses present in a time-gated portion 54 of the waveform plot in the A-scan window. The amplitude within the time-gated portion can be derived from a smoothed and integrated function of the waveform plot according to known mathematical principles. For example, smoothed and integrated functions are show as dashed curves and their corresponding waveform plots are shown as solid curves in FIGS. 4 and 6. The time-gated portion 54 in FIG. 2 is selected according to considerations that may be understood by considering FIGS. 3-6.

The C-scan window of FIG. 3 displays the same C-scan image as that of the C-scan window 30 in FIG. 2, however, the cross-hair cursor 32 is disposed over a different pixel which corresponds to a different particular sensor and therefore a different location of an inspected structure. In FIG. 2, the cross-hair cursor in the C-scan window is disposed at a pixel in the damaged portion 38 and the waveform plot in the A-scan window represents the electrical signal generated when the corresponding sensor received an echo signal from the damaged portion of the inspected structure. In FIG. 3 the cross-hair cursor in the C-scan window is disposed at a pixel in the undamaged background area 42 and the waveform plot in the A-scan window of FIG. 4 represents the electrical signal generated when the corresponding sensor received an echo signal from the undamaged area of the inspected structure.

The axes of the A-scan window of FIG. 4 are expanded compared to the A-scan window of FIG. 2 in order to better display the time-gated portion 54 of the waveform plot. In FIG. 4, the waveform pulse 56 preceding the time-gated portion 54 represents an echo pulse returning to the sensor from the front surface, which is that surface facing the sensor array, of an inspected structure. The waveform pulse 58 represents an echo pulse returning to the sensor from the back surface of the structure opposite the sensor array. Relative quiescence in the time-gated portion 54 reveals that the material of the structure between the front and back surfaces is relatively free of discontinuities and is likely undamaged. The coloration of the pixel under the cross-hair cursor 32 in FIG. 3 is related to relatively low amplitudes of minor waveform pulses in the time-gated portion 54. Waveform plots corresponding to other pixels in the undamaged background area 42 would demonstrate similar relative quiescence in their time-gated portions 54. The time-gated portion 54 is selected to correspond to the material of the structure between the front and back surfaces.

The C-scan window of FIG. 5 also displays the same C-scan image as that of the C-scan window 30 of FIG. 2. In FIG. 5, the cross-hair cursor 32 is disposed over a pixel in the damaged portion 40. Note the presence of echo pulses within the time-gated portion 54 of FIG. 6. These echo pulses, and those present in the time-gated portion 54 of the A-scan window 30 in FIG. 2, reveal that the structure locations corresponding to the pixels under the cross-hair cursor in FIGS. 2 and 5 are damaged. Because quiescence is not observed in the time-gated portions of the A-scans in FIGS. 2 and 5, it can be deduced that echo pulses have reflected from discontinuities between front and back surfaces of the inspected structure. Such discontinuities in this context are correlated with damage.

The pixels in the C-scan images of FIGS. 2, 3, and 5 are each colored according to the summed amplitudes of echo pulses present in time-gated portions of corresponding waveform plots. Thus, these images are C-scan echo amplitude images that represent the total ultrasonic echo energy reflected from discontinuities between the front and back surfaces of an inspected structure. Pixels having colors that differ from the undamaged background area 42 generally correspond to damaged locations within the inspected structure. The damage revealed by the pixels in the damaged areas 38 and 40 resides between the front and back surfaces of the inspected structure. The areas 38 and 40 graphically display images of the damage. The size, disposition, and severity of the damage are revealed by the sizes, dispositions, and colorations of the areas 32 and 40 in the C-scan image.

The B-scan window 28 in FIG. 2 displays a cross-section depth image of a portion of the structure under inspection. The image was collected by sensors corresponding to the row 34 of pixels in the C-scan window 30. Sensor positions are represented along a horizontal axis 60 and the depths of echo reflecting features such as damage are represented along a vertical axis 62. Each pixel within the image is colored according to the amplitude of any echo pulse received by the corresponding sensor from the corresponding depth. Depth is derived from the time of flight (TOF) measured between the dispatch of an ultrasonic pulse into a structure and the return of an echo pulse. If the speed of propagation of ultrasonic pulses is known for a particular inspected material, the vertical axis 62 can be calibrated toward particular linear depth dimensions according to the TOF of each echo pulse. The vertical axis can also be empirically calibrated using a material sample having a calibrated depth. Otherwise, the vertical axis can be treated as a relative depth axis without specific linear dimensions and can simply be treated as a TOF axis.

However the vertical axis is calibrated or treated, the B-scan image in the window 28 represents a cross-section view of the structure taken along the row of sensors corresponding to the row 34 of pixels in the C-scan window. A portion 38 of the B-scan image corresponds to a horizontal slice of the damaged portion 38 displayed in the C-scan window. Similarly, a portion 40 of the B-scan image corresponds to a horizontal slice of the damaged portion 40 of the C-scan image. Between the portions 38 and 40 of the B-scan image, a horizontal slice of the undamaged background area 42 is shown. Thus, an operator may view the echo-amplitude image in the C-scan window 30 to appreciate a plan view image of damages, and then view the cross-section depth image in the B-scan window 28 to appreciate a view of the depth distribution of the damage within the inspected structure taken along a horizontal slice.

The B-scan window 26 in FIG. 2 similarly displays a cross-section depth image of a portion of the structure under inspection. The image was collected by sensors corresponding to the column 36 of pixels in the C-scan window 30. Sensor positions are represented along a vertical axis 64 and the depths of echo reflecting features such as damage are represented along a horizontal axis 66. Each pixel within the image is colored according to the amplitude of any echo pulse received by the corresponding sensor from the corresponding depth. The portion 38 of the B-scan image in the window 26 corresponds to a vertical slice of the damaged portion 38 displayed in the C-scan window 30. Thus, an operator may view the cross-section depth image in the B-scan window 26 to appreciate a view of the depth distribution of the damage within the inspected structure taken along a vertical slice.

In FIG. 2, as an operator manipulates a user interface device such as a movable mouse device or a keypad having directional keys, the cross-hair cursor 32 is disposed at varying locations within the C-scan window 30. As the cursor is disposed at any particular pixel, the A-scan window 24 displays a waveform plot representing an electrical signal generated by the sensor corresponding to the particular pixel. Furthermore, the B-scan windows 28 and 26 display depth images taken along the corresponding row and corresponding column of sensors respectively as the cursor is moved about. The data for the various views is generally first collected by the ultrasonic inspection system 10 (FIG. 1) and is then viewed and analyzed by an operator. Nonetheless, an operator may prompt the collection of new pulse echo data for any particular sensor or for the entire array by manipulating virtual controls available on the display screen shown in FIG. 2.

The descriptions herein refer to rows and columns of sensors and pixels distributed along horizontal and vertical axes as a convenient convention in describing two dimensional arrangements of sensors and pixels. It should be understood that the flexible sensor array 12 can be disposed across an area of a structure in almost any arbitrary orientation. Thus, the described axes need not correspond to any vertical axis demonstrated by a plumb line or any horizontal axis such as those along the floor of a hangar where aircraft are inspected.

Furthermore, the B-scan and C-scan images of the figures generally relate greater echo pulse amplitudes to darker pixel colorations as another convenient convention for the purpose of illustrating subjects of these descriptions. Lighter pixel colorations could just as well be related to greater echo pulse amplitudes in an alternative convention. Indeed, the correlation of the amplitude of an echo pulse to the coloration of a corresponding pixel can be selected according to any desired function or mapping and a color legend may be provided. Though the figures described herein generally provide black and white images, these descriptions relate as well to images comprising pixels having any number of colors such as blue, green, yellow, and red. These descriptions relate to almost any pixel coloring convention, shading convention, or pixel character convention by which an operator may discern information provided by graphically displayed pixels.

A specific example of inspection activities concerning a damaged aircraft structure is illustrated in FIGS. 7-9. FIG. 7 illustrates a composite panel 70, which comprises a generally planar skin 72 and an underlying channel member 74 having spaced parallel flanges 73 and 75 bonded to the back surface of the skin along bond areas 76 and 78. In the aircraft industry, such channel members are often called stiffeners, stringers, and trapezoidal hat stringers. If the bonding of the flanges to the skin is lost or compromised, the benefits of the channel member toward strengthening and stiffening the composite panel can be diminished. However, the skin is typically disposed along a front, outward, or available surface of an aircraft structure and the channel member is typically hidden or internal. The bonding of the flanges to the skin can nonetheless be inspected according to the present invention.

In FIG. 7, a marked area 80 along the skin 72 represents an area where damage is suspected. For example, a ground maintenance vehicle may have inadvertently impacted the skin 72 leaving the visibly marked area 80 that raises the concerns of a ground crew inspecting the aircraft structure. In FIG. 8, the flexible sensor array 12 is disposed across the area where damage is suspected. Each sensor of the array is successively energized and amplitude and time data for returning echo pulses are collected. In FIG. 9, a C-scan image of the area under the flexible sensor array is provided. Upon viewing the C-scan image, an operator may appreciate that the affected area, as indicated by a pixel group 88, may be smaller in extent than the marked area 80 visible on the skin 72 in FIG. 7.

The nature of the data presented in the C-scan image in FIG. 9 differs from that of the C-scan images in FIGS. 2, 3, and 5, which are echo amplitude images revealing summed echo energy received from a selected depth range. The C-scan image in FIG. 9 is a C-scan depth image wherein pixels are colored according the depths from which the echo pulses having the greatest amplitudes are reflected. The corresponding A-scan waveform plots are time-gated to exclude reflections from the top surface of the inspected structure. For each sensor, which corresponds to a particular pixel, a number of echo pulses may be received. The time of flight (TOF) of that echo pulse having the greatest amplitude is used to derive the depth of the discontinuity from which the echo pulse reflected. Thus, the color of each pixel reveals the depth of a relatively severe discontinuity under the top surface of the inspected structure at the location of the corresponding sensor. In FIG. 9, the color convention is selected to present the deepest discontinuities in the darkest colors. In particular, colors 111, 112, 113, and 114 are arranged along a color legend 115 and represent increasingly deep discontinuities. For example, the color 113 corresponds to the depth of the skin 72 and the color 114 corresponds to the summed depth of the skin 72 and flange 75. The colors 111 and 112 correspond to shallow depths that are less than the depth of the skin.

The upper and lower bands 82 and 84 in the C-scan image of FIG. 9 correspond to the sensors of the flexible sensor array that are disposed beyond the bond area 78 in FIG. 8. These sensors receive echo pulses from the back surface of the skin 72 in areas where the flanges 75 of the channel member are not present. Thus, the color 113 of the corresponding pixels reveals the depth of the skin and reveals that discontinuities such as damage are not likely present in these bands. The central band 86 in the C-scan image of FIG. 9 corresponds to the bond area 78 where one of the flanges 75 is bonded to the back surface of the skin. Thus, the color 114 of the corresponding pixels generally reveals the summed depths of the skin and flange.

The lighter pixel group 88 within the central band 86 of FIG. 9, however, reveals that damage resides within the skin along the bond area 78. Thus, the pixel group within the C-scan image defines a depth image of the damage. The pixel group reveals a dimple-shaped damage within the skin. A central pixel group having the color 112 is surrounded by an approximately annular pixel group having the color 111. Thus, these pixel groups represent an annular damage area surrounding a deeper core damage area.

In order to further investigate the damage revealed in FIG. 9, an operator may further view the B-scan images provided in FIGS. 10 and 11. Like the B-scan images in FIG. 2, the B-scan images in FIGS. 10 and 11 display cross-section depth images of portions of the structure under inspection. In particular, the B-scan image in FIG. 10 displays a depth image of an undamaged portion of the composite panel 70 and the B-scan image in FIG. 11 displays a depth image of a damage portion. In FIGS. 10 and 11, depth is represented along vertical axes. Pixels corresponding to sensors in columns 90 and 92 of the sensor array 12 in FIG. 8 are disposed along horizontal axes in FIGS. 10 and 11 respectively. Dark bands 94 and 96 stretching horizontally across the images in FIGS. 10 and 11, respectively, represent the front surface of the skin 72 along the columns 90 and 92 in FIG. 8. Deeper dark bands 98 and 100 in FIG. 10 represent the back surface of the skin at sensor positions along the column 90 beyond the bond area 78. The deepest dark band 102 in FIG. 10 represents the back of the flange 75. The lack of dark colorations between the band 102 and the band 94 reveals relative quiescence with regard to echo pulses from the structure between the front surface of the skin and the back surface of the flange along the bond area. This supports corresponding evidence along the column 90 in FIG. 9 in revealing that the structure along the column 90 is not likely damaged.

FIG. 11 displays deeper dark bands 104 and 106 that represent the back surface of the skin at sensor positions along the column 92 beyond the bond area 78 in FIG. 8. However, the back surface of the flange 75 along the column 92 is not well represented by a dark band area in FIG. 11. Instead, shallow damages apparently disposed between the front and back surfaces of the skin are represented by the band 108 in FIG. 11. This supports corresponding evidence along the column 92 in FIG. 9. Thus, an operator may view FIGS. 10 and 11 to appreciate cross-section depth views along undamaged and damaged portions of the composite panel 70 in FIG. 8. In FIGS. 10 and 11, each pixel is colored according to the amplitude of any echo pulse received by the corresponding sensor from the corresponding depth, which is derived from the time of flight of the echo pulse. The B-scan images of the FIGS. 10-11 generally relate greater echo pulse amplitudes to darker pixel colorations and several pixel colorations representing respective amplitude ranges are displayed. An operator viewing FIG. 11 may appreciate the severity of the revealed damage by discerning the several pixel colorations and by obtaining an understanding of the correlation of the amplitude of an echo pulse to the coloration of a corresponding pixel. Such an understanding may be obtained, for example, through experience and by way of viewing a color legend A particularly advantageous and inventive method of displaying an image of a damage comprises displaying a threshold image of damage wherein each pixel is colored one of only two colors. For example, FIGS. 12 and 13 correspond to FIGS. 10 and 11 respectively such that the only differences reside in the correlation of the amplitude of an echo pulse to the coloration of a corresponding pixel. FIGS. 12 and 13 provide threshold images of the composite panel structure along the sensor columns 90 and 92, respectively in FIG. 8. In rendering the images in FIGS. 12 and 13, a threshold for darkening pixels correlated with a particular echo-pulse amplitude has been selected by an operator or automatically by the ultrasonic inspection system according to embodiments of the present invention. Darkened pixels correspond to sensors that received echo pulses having amplitudes greater than the selected threshold. The threshold may be selected according to a predetermined criterion and may be selected tentatively as an operator seeks to visualize and characterize damages. Thus, minor discontinuities in the inspected structure may be at least tentatively ignored so that an operator may concentrate inspection efforts and concerns toward only the more significant discontinuities that give rise to echo pulses above the selected threshold. This advantage may serve to reduce operator training, to minimize inspection errors, to standardize interpretation approaches, to promote objectivity in selecting modes of returning an aircraft to service, and to promote the application of predetermined criteria in determining damage characteristics.

FIGS. 14-19 provide corresponding pairs of C-scan images. The images may be echo amplitude images and may be depth images in the context of these descriptions. In any event, FIGS. 14-16 correspond respectively to FIGS. 17-19. In FIGS. 14-16, several pixel colorations are provided and the darkest of the pixels generally reveal damages within an inspected structure. In FIGS. 17-19, wherein each pixel is colored one of only two colors, the damage evident in each of FIGS. 14-16 is displayed in threshold images. An operator, a business entity, or a government entity may prefer the threshold images in determining damage characteristics of damage, for example, in situations where it is desirable to determine whether damage satisfies predetermined criteria.

In some situations, it may be desirable to determine whether damage satisfies a predetermined criterion that defines a predetermined linear dimension such as a predetermined depth or a predetermined length. For example, in FIG. 17, a longest chord 122 of the damage 120 is measured between the two most distant pixels within the image of the damage. In this example, determining whether damage satisfies a predetermined linear dimension comprises determining whether the longest chord exceeds a predetermined length.

In some situations, it may be desirable to determine whether a damage satisfies a predetermined criterion that defines a predetermined area. For example, in FIG. 18, a longest chord 126 and a second chord 128 are measured in order to determine an area measurement of damage 124 by multiplication of the two chords. The second chord spans the largest part of the damage along an axis that is perpendicular to the longest chord. In this example, determining whether damage satisfies a predetermined criterion comprises determining whether such an area measurement exceeds a predetermined area. In some situations, it may be desirable to determine whether a damage cluster satisfies a predetermined criterion such as a predetermined area. For example, in FIG. 19, a longest chord 130 and a second chord 132, which is perpendicular to the longest chord, are measured in order to determine an area encompassing the damage cluster.

An aspect of the present invention relates to a method of inspecting an aircraft structure. In an embodiment represented in FIG. 20, the method 200 is preceded by the occurrence 201 of a damage event such as that which occurs when a maintenance vehicle or maintenance personnel inadvertently contacts an aircraft structure or, for example, when an aircraft is attacked by gunfire. The method 200 comprises the step 202 wherein an ultrasonic inspection system, such as the system 10 of FIG. 1, is set up for inspecting the aircraft structure. This step can entail, for example, establishing the speed of propagation of ultrasonic pulses in the inspected material in order to correlate TOF measurements with material depths, and optionally disposing a flexible sensor array onto a sample structure in order to select, adjust, or calibrate time and depth axes ranges and time-gate settings for A-scan, B-scan, and C-scan windows.

In step 204, a two dimensional array of pulse-echo sensors, such as the flexible sensor array 12 of FIG. 1, is disposed across the aircraft structure at the location of the suspected damage, for example, as shown in FIG. 8. This may entail activating a vacuum system in order to tentatively adhere the array to the structure. In step 206, individual sensors of the array generate ultrasonic pulses which enter the structure in step 208 causing echo signals to return to the sensors in step 210. In step 212, the sensors generate electrical signals upon receipt of the echo signals. In step 214, the electrical signals generated by the sensors are stored as amplitude time data.

In step 216, the amplitude and time data is displayed, for example as one or more A-scan waveform plots as shown in FIG. 6. Furthermore, in step 216 scan types such as B-scans and C-scans are selected for use in inspecting the structure. These selections can be made by an operator or may be made automatically by a computing and display device such as device 16 in FIG. 1. For example, in one embodiment of the invention, as the computing and display device 16 initializes for use, the A-scan window 24, the B-scan windows 26 and 28, and the C-scan window 30 are automatically relatively sized and disposed as shown in FIG. 2.

In step 218, thresholds are selected and TOF data is correlated with depth. Thresholds can be automatically selected according to one or more predetermined criteria or may be selected and adjusted by an operator. TOF data can be correlated with depth according to the set-up established in step 202.

In step 220, one or more images of the damage to the inspected structure are graphically displayed. Each displayed image is defined by a respective two-dimensional matrix of pixels each corresponding to a particular sensor. For example, a C-scan image may be displayed wherein each pixel uniquely corresponds to a particular sensor in a one-to-one correspondence. For further example, a B-scan image may be displayed wherein each row or column of pixels is correlated to a particular sensor. Furthermore in step 220, the damage is measured. For example, the depth of the damage, the area of the damage, and linear dimensions such as chords may be measured as shown in FIGS. 17-19.

In step 222, a determination is made as to whether the damage satisfies one or more predetermined criteria. This can include determining whether the depth of a damage exceeds a predetermined depth criterion, or as described above with reference to FIGS. 17-19, this can include determining whether lengths and areas exceed predetermined criteria. In any event, in step 222, a mode of returning the inspected aircraft structure to flying service is selected in step 222 based on the determination of whether the damage satisfies one or more predetermined criteria.

In the embodiment of the inventive method represented in FIG. 20, the available modes of returning an aircraft structure to flying service include three modes available for selection. These may be considered in an order according to increasing repair efforts and resources prescribed by the modes. First in the order, in step 224, if the damage is considered to be minimal, no repair is selected and the aircraft structure is returned to flying service in step 236. For example, it may be determined that length, depth, and area measurements of the damage are less than respective predetermined criteria and the aircraft structure may be promptly returned to flying service.

Second in the order, in step 226, the damage is considered to require some attention and a rapid repair mode is selected. For example, the measured length, depth, and area of a damage may each fall between low and high predetermined respective criteria. In such circumstances, a bonded repair mode entailing adhesively bonding a patch onto the surface of the inspected structure may be selected.

Third in the order, in step 228, the damage is considered to require more extensive repair. The aircraft structure is taken tentatively off-line with regard to flying service and a thorough repair is made. For example, a lay-up repair mode may be selected wherein some portion of the damaged material is removed by sanding or grinding and layers of replacement material are bonded in succession to effect a layered repair to the parent material. For further example, a bolted repair mode may be selected wherein portions of the aircraft structure are removed and corresponding replacement components are bolted or riveted into place.

Following repairs, whether rapid or extensive repair modes were selected, each of step 226 and 228 are followed by step 230 wherein the repair is inspected. For example, a two dimensional array of pulse-echo sensors, such as the flexible sensor array 12 of FIG. 1, may be disposed across the aircraft structure at the location of the repair and an image of the repair may be graphically displayed to an operator. In step 232, the quality of the repair is determined. For example, the operator may determine whether voids or undesirable porosities are present at the location of the repair. If the quality of the repair is determined adequate in step 232, the aircraft structure is returned to flying service in step 236. On the other hand, if the quality of the repair is determined inadequate in step 232, one or more additional repairs are made in step 234, after which, the inventive method returns to step 230 wherein the additional repair is inspected.

The ultrasonic inspection system 10 (FIG. 1) could be used to inspect any number of aircraft structures in a variety of commercial and military facilities where the detection of flaws or defects in a structure is required. Examples of such flaws and defects include, but are not limited to: impact damages such as delaminations and matrix cracking; disbonds in airframe reinforcing members or honeycomb composites; and discontinuities including voids and areas having undesirable porosity. In addition, the sensors could be utilized for various other purposes, such as for identifying ply count or thickness.

Activities toward inspecting an aircraft structure can be divided among technicians and analysts at separate locations. For example, a technician at the location of an aircraft may dispose a sensor array onto a structure of the aircraft and an analyst at a distal location may receive and analyze the collected data. In this situation, determinations whether damages satisfy criteria, and selections toward modes of returning a damaged aircraft structure to flying service can be accomplished far from the aircraft structure and instructions toward the returning the aircraft to service can be transmitted back to the technician. This may be advantageous with regard to utilizing experienced personnel in analyzing the data and interpreting images of damages.

The term "structure" may not be construed toward limiting the scope of these descriptions. These descriptions relate to inspection sensors, systems, and methods that can be used to inspect any number of parts or structures of different shapes and sizes, such as machined forgings, castings, pipes, or composite panels or parts. Inspections can be performed on newly manufactured structures or existing structures that are being inspected for preventative maintenance purposes. In addition, an inspected structure can include various components. For instance, an inspected structure can include a substructure for providing additional support to the structure. Further, an inspected structure can include any number of materials. For example, an inspected structure can include a metallic material, such as aluminum, or a composite material, such as graphite-epoxy. Moreover, an inspected structure can be a component of an aircraft, such as a Boeing Dreamliner 787, which has components such as a fuselage and wings that comprise composite materials.

Furthermore, the term "structure" as used herein relates to aircraft structures and other structures as well, including composite structures such as bridges and boats. For example, after an automobile accident under a bridge, a composite support column of a bridge may have markings indicating an impact to the column. An ultrasonic inspection system such as the system 10 (FIG. 1) may be used to inspect the column by placement of the flexible sensor array 12 upon the surface of the column in order to measure the size and depth of damage to the column. A temporary repair may be made to the column and traffic may be permitted to pass the bridge. An additional repair, which may be a more extensive or more permanent repair, may be made at a later time when traffic volume is low. As previously stated, these descriptions relate to a sensor array having any number of sensors arranged in any two-dimensional pattern. Thus, these descriptions relate to sensor arrays having large areas to permit efficient inspections of large structures such as roadway structures like roadbeds and bridges.

In another example, after a boat impacts an object, the hull of the boat can be inspected in order to assess damage caused by the impact. The boat may, for example, impact a dock, a log, a rock, another water craft, or other object. An ultrasonic inspection system such as the system 10 (FIG. 1) may be used to inspect the boat by placement of the flexible sensor array 12 upon a surface of the boat, for example the hull of the boat. Ultrasonic inspection of the hull of the boat can proceed without removing the boat from water. As the leading edge of the hull of a boat is particularly subject to impacting objects when the boat is in motion, flexibility of the sensor array permits the array to wrap closely about the leading edge. On the other hand, the sensor array can be manufactured to have a crease to receive the leading edge. For example, a particular sensor array can be manufactured to have a crease with a radius of curvature and inner defined angle to match the dimensions of the leading edge of a particular boat or range of boats.

Many modifications and other embodiments of the invention set forth herein will come to mind to one skilled in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A method of inspecting an aircraft structure, the method comprising:

disposing a two-dimensional array of ultrasonic pulse-echo sensors onto a surface of an aircraft structure;

sending from each particular sensor an ultrasonic pulse into the surface;

receiving by each particular sensor an ultrasonic echo signal resulting from the sending of the ultrasonic pulse by the particular sensor;

graphically displaying an image of damage within the aircraft structure, wherein graphically displaying an image of the damage comprises displaying a C-scan image defined by a two-dimensional matrix of pixels each of which uniquely corresponds to a particular one of the sensors in a one-to-one correspondence, determining a position of a cursor in correspondence to a respective pixel of the C-scan image, and graphically displaying first and second B-scan images comprising cross-sectional depth images derived from data collected by respective pluralities of sensors that are at least partially defined by the position of the cursor and that are arranged in two different directions;

determining whether the damage satisfies a predetermined criterion; and selecting a mode of returning the aircraft structure to flying service based on the determination of whether the damage satisfies a predetermined criterion.

2. The method of claim 1, wherein the predetermined criterion defines a predetermined linear dimension, and wherein determining whether the damage satisfies the predetermined criterion comprises determining a measurement of a linear dimension of the damage and determining whether the measurement exceeds the predetermined linear dimension.

3. The method of claim 2, wherein the predetermined criterion defines a predetermined length, and wherein determining whether the damage satisfies the predetermined criterion comprises determining a length measurement of the damage and determining whether the length measurement exceeds the predetermined length.

4. The method of claim 3, wherein determining a length measurement of the damage comprises determining a longest chord measurement of the damage.

5. The method of claim 2, wherein the predetermined criterion defines a predetermined depth, and wherein determining whether the damage satisfies the predetermined criterion comprises determining a depth measurement of the damage and determining whether the depth measurement exceeds the predetermined depth.

6. The method of claim 1, wherein the predetermined criterion defines a predetermined area, and wherein determining whether the damage satisfies the predetermined criterion comprises determining an area measurement of the damage and determining whether the area measurement exceeds the predetermined area.

7. The method of claim 6, wherein determining an area measurement of the damage comprises determining a longest chord measurement of the damage and a second chord perpendicular to the longest chord.

8. The method of claim 7, wherein the first longest chord measurement and the second chord measurement define an area encompassing a damage cluster.

9. The method of claim 1, wherein graphically displaying an image of the damage comprises displaying a threshold image wherein each pixel of the matrix is colored one of only two colors.

10. The method of claim 1, further comprising determining a time of flight of an echo pulse within each ultrasonic echo signal by measuring for each sensor the time elapsed between sending the ultrasonic pulse and receiving the echo pulse, wherein each pixel of the matrix is colored to represent the determined time of flight of the echo pulse for the sensor to which the pixel uniquely corresponds such that the C-scan image defines a depth image of the damage.

11. The method of claim 10, wherein each ultrasonic echo signal received comprises one or more echo pulses, and wherein determining a time of flight of an echo pulse within each ultrasonic echo signal comprises determining the time of flight of the greatest amplitude echo pulse within each ultrasonic echo signal.

12. The method of claim 1, wherein selecting a mode of returning the aircraft structure to flying service comprises selecting a mode of repairing the damage, the method further comprising:

making a repair to the damage according to the selected mode of repairing;

disposing at least one ultrasonic sensor onto the surface at the location of the repair;

graphically displaying an image of the repair, the image defined by a matrix of pixels; and determining the quality of the repair based on the displayed image of the repair.

13. The method of claim 12, wherein determining the quality of the repair comprises determining whether an additional repair is needed, the method further comprising:

making an additional repair; and disposing at least one ultrasonic sensor onto the surface at the location of the additional repair.

14. A method of selecting a mode of returning a damaged aircraft structure to flying service, the method comprising:

graphically displaying an image of damage within an aircraft structure, the image representing signals generated by a two-dimensional array of sensors disposed across a surface of the aircraft structure, wherein graphically displaying an image of the damage comprises displaying a C-scan image comprising a two dimensional matrix of pixels each of which uniquely corresponds to a particular one of the sensors in a one-to-one correspondence, determining a position of a cursor in correspondence to a respective pixel of the C-scan image, and graphically displaying first and second B-scan images comprising cross-sectional depth images derived from data collected by respective pluralities of sensors that are at least partially defined by the position of the cursor and that are arranged in two different directions;

determining whether the damage satisfies a first predetermined criterion;

determining whether the damage satisfies a second predetermined criterion; and selecting a mode of returning the aircraft structure to flying service based on the determinations of whether the damage satisfies the first and second predetermined criteria, wherein selecting the mode of returning the aircraft structure to flying service comprises selecting, based upon the determinations of whether the damage satisfies the first and second predetermined criteria, to: (i) return the aircraft structure to flying service without repair, (ii) return the aircraft structure to flying service following a repair and without taking the aircraft structure off-line with regard to flying service and (iii) return the aircraft structure to flying service after taking the aircraft structure off-line with regard to flying service in order to effect a repair.

15. The method of claim 14, further comprising measuring a longest chord of the damage, wherein the first predetermined criterion defines a predetermined first length, and wherein the second predetermined criterion defines a predetermined second length.

16. The method of claim 15, wherein determining whether the damage satisfies a first predetermined criterion comprises determining whether the longest chord exceeds the predetermined first length, and wherein determining whether the damage satisfies a second predetermined criterion comprises determining whether the longest chord exceeds the predetermined second length.

17. The method of claim 14, further comprising measuring a linear dimension of the damage, wherein the first predetermined criterion defines a predetermined first linear dimension, and wherein the second predetermined criterion defines a predetermined second linear dimension.

18. The method of claim 17, wherein selecting a mode of returning the aircraft structure to flying service comprises:
    returning the aircraft structure to flying service without making a repair if the linear dimension of the damage is less than the predetermined first linear dimension;
    making a first level repair if the linear dimension of the damage is greater than the predetermined first linear dimension and is less than the predetermined second linear dimension;
    making a second level repair, which second level repair is more extensive than the first level repair, if the linear dimension of the damage is greater than the predetermined second linear dimension.

19. The method of claim 18, wherein making a first level repair comprises applying a single adhesive patch, and wherein making a second level repair comprises applying multiple layers of material.

20. The method of claim 17, wherein measuring a linear dimension of the damage comprises measuring a depth of the damage, wherein the first predetermined criterion defines a predetermined first depth, and wherein the second predetermined criterion defines a predetermined second depth.

21. A method of selecting a mode of returning a damaged aircraft structure to flying service, the method comprising:
    receiving data based on signals generated by a two-dimensional array of sensors that was disposed across a surface of an aircraft structure;
    graphically displaying an image of damage within the aircraft structure, the image based on the received data, wherein graphically displaying an image of the damage comprises displaying a C-scan image comprising a two dimensional matrix of pixels each of which uniquely corresponds to a particular one of the sensors in a one-to-one correspondence, determining a position of a cursor in correspondence to a respective pixel of the C-scan image, and graphically displaying first and second B-scan images comprising cross-sectional depth images derived from data collected by respective pluralities of sensors that are at least partially defined by the position of the cursor and that are arranged in two different directions;
    determining whether the damage satisfies a predetermined criterion;
    selecting a mode of returning the aircraft structure to flying service based on the determination of whether the damage satisfies a predetermined criterion; and
    transmitting an indication of the selected mode.

22. The method of claim 21, wherein selecting a mode of returning the aircraft structure to flying service comprises selecting a mode of making a repair, the method further comprising receiving additional data based on signals generated by at least one sensor disposed across a repair made according to the selected mode of making a repair.

23. The method of claim 22, further comprising:
    graphically displaying an image of the repair based on the additional data; and
    determining the quality of the repair based on the displayed image of the repair.

24. The method of claim 21, the image is graphically displayed by a display device that is not co-located with the aircraft structure.

25. A method of inspecting a structure, the method comprising:
    disposing a two-dimensional array of ultrasonic pulse-echo sensors onto a surface of a structure;
    sending from each particular sensor an ultrasonic pulse into the surface;
    receiving by each particular sensor an ultrasonic echo signal resulting from the sending of the ultrasonic pulse by the particular sensor;
    graphically displaying an image of damage within the structure, the image defined by a two-dimensional matrix of pixels each of which corresponds to a particular one of the sensors, wherein graphically displaying an image of the damage comprises displaying a C-scan image comprising a two dimensional matrix of pixels each of which uniquely corresponds to a particular one of the sensors in a one-to-one correspondence, determining a position of a cursor in correspondence to a respective pixel of the C-scan image, and graphically displaying first and second B-scan images comprising cross-sectional depth images derived from data collected by respective pluralities of sensors that are at least partially defined by the position of the cursor and that are arranged in two different directions;
    determining whether the damage satisfies a predetermined criterion; and
    selecting a mode of returning structure to usage based on the determination of whether the damage satisfies a predetermined criterion.

26. The method of claim 25, wherein disposing a two-dimensional array of ultrasonic pulse-echo sensors onto a surface of a structure comprises disposing the array onto a surface of a composite structure.

27. The method of claim 26, wherein disposing the array onto a surface of a composite structure comprises disposing the array onto a bridge.

28. The method of claim 27, wherein selecting a mode of returning the structure to usage comprises selecting a mode of repairing the damage, the method further comprising:
    making a repair to the damage according to the selected mode of repairing; and
    permitting vehicle traffic to pass over or under the bridge.

29. The method of claim 28, further comprising, after making the repair permitting vehicle traffic to pass over or under the bridge, making an additional repair to the damage at a time when vehicle traffic is low.

30. The method of claim 26, wherein disposing the array onto a surface of a composite structure comprises disposing the array onto a surface of a boat.

31. The method of claim 30, wherein disposing the array onto the leading edge of a hull of a boat.

32. The method of claim 30, wherein the array is disposed onto a surface of the boat while the boat floats in water.

* * * * *

UNITED STATES PATENT AND TRADEMARK OFFICE
CERTIFICATE OF CORRECTION

PATENT NO. : 7,617,730 B2 Page 1 of 1
APPLICATION NO. : 11/427108
DATED : November 17, 2009
INVENTOR(S) : Gary E. Georgeson It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 642 days.

Signed and Sealed this

Nineteenth Day of October, 2010

David J. Kappos
*Director of the United States Patent and Trademark Office*